June 11, 1974 G. BUCKNER Plant Pat. 3,566
ROSE PLANT
Filed Jan. 8, 1973
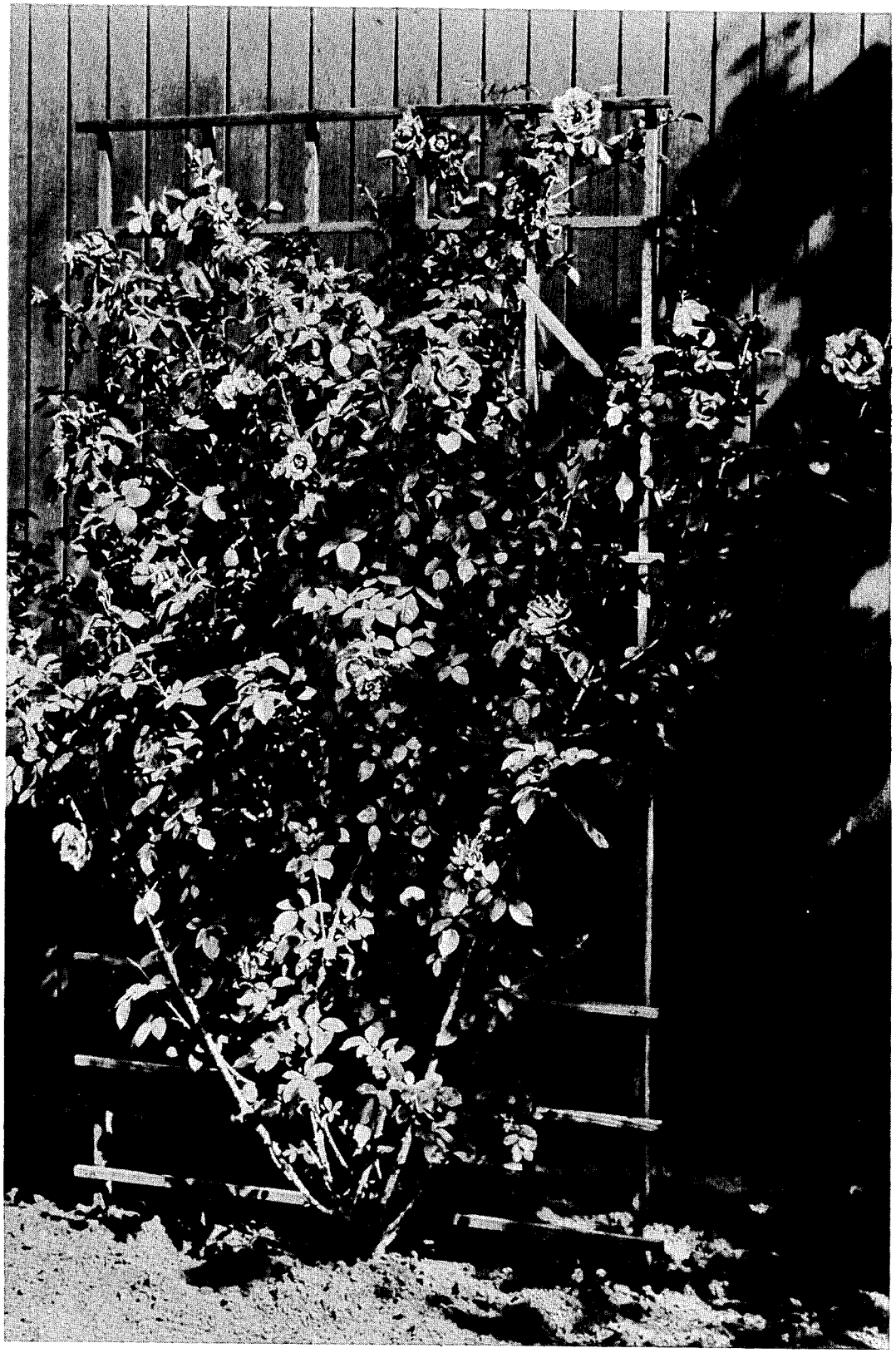

United States Patent Office

Plant Pat. 3,566
Patented June 11, 1974

3,566
ROSE PLANT

George Buckner, Tyler, Tex., assignor to Jackson & Perkins Company, Medford, Oreg.

Filed Jan. 8, 1973, Ser. No. 321,678
Int. Cl. A01g 5/00
U.S. Cl. Plt.—2 1 Claim

The present invention relates to a new and distinct variety of rose plant of the climber class, which was discovered by me as a sport of the variety Orchid Masterpiece, U.S. Plant Pat. 2,039.

At the time of my discovery aforementioned, I was in charge of the growing of a large block of plants of the bush rose variety, Orchid Masterpiece being grown under license from the owner, Jackson & Perkins Co., of U.S. Plant Pat. 2,039, issued Mar. 28, 1961.

In the course of one of my inspections of these fields, my attention was attracted to one plant on which appeared a climbing branch. Upon close examination of this plant, I found that it had sported and I thereupon promptly took steps to preserve the sport, keep it under observation, and to asexually reproduce the same by budding, as performed at Tyler, Tex., and at Wasco, Calif., for the purpose of determining whether its climbing habit was fixed and transmissible by asexual reproductions. The climbing habit was fully confirmed and transmitted through several propagations.

The parent variety Orchid Masterpiece is a popular rose variety of the bush type, hybrid tea class, but so far as I am aware, it has never previously exhibited a climbing habit and its growth has been that of the average bush rose.

The new variety is substantially identical in all respects to its parent, except that it is definitely a climber, as evidenced by its long, strong canes which attain a mature length of at least ten feet or more. In view of the general similarities between the new sport variety and its parent, except as noted in the foregoing, it is unnecessary to specifically describe the new variety in detail herein, since it otherwise substantially conforms to the detailed description embodied in Pl. Pat. 2,039 to which reference may be readily had. However, for convenience, the accompanying illustration has been presented to indicate the climbing habit of growth of the new variety.

I claim:

1. A new and distinct variety of rose plant of the climber class, substantially as herein shown and described, characterized particularly as to novelty by being substantially identical with its parent variety, Orchid Masterpiece, U.S. Pl. Pat. 2,039, but being distinguished therefrom by its long, strong canes which attain a mature height of at least ten feet or more, indicative of its climbing habit of growth.

No references cited.

ROBERT E. BAGWILL, Primary Examiner